(12) United States Patent
Rando et al.

(10) Patent No.: US 6,887,879 B2
(45) Date of Patent: *May 3, 2005

(54) PHARMACEUTICAL COMBINATION OF ANTIVIRAL AGENTS

(75) Inventors: Robert F. Rando, Beaconsfield (CA); Zhengxian Gu, Quebec (CA)

(73) Assignee: Shire BioChem Inc., Laval (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/146,027

(22) Filed: May 16, 2002

(65) Prior Publication Data

US 2003/0045534 A1 Mar. 6, 2003

Related U.S. Application Data

(62) Division of application No. 09/515,328, filed on Feb. 29, 2000, now Pat. No. 6,511,983.
(60) Provisional application No. 60/122,480, filed on Mar. 1, 1999.

(51) Int. Cl.$^7$ .............. A61K 31/70; A61K 31/52; A61K 31/50; A61K 31/147; A61K 31/425
(52) U.S. Cl. ............ 514/262; 514/50; 514/226; 514/253.01; 514/307; 514/365
(58) Field of Search ............ 514/262, 50, 266, 514/220, 253.1, 307, 365

(56) References Cited

U.S. PATENT DOCUMENTS

| | | | |
|---|---|---|---|
| 4,724,232 A | * 2/1988 | Rideout et al. | 514/50 |
| 5,041,449 A | 8/1991 | Belleau et al. | 514/274 |
| 5,179,104 A | 1/1993 | Chu et al. | 544/310 |
| 5,270,315 A | * 12/1993 | Belleau et al. | 514/262 |
| 5,276,151 A | 1/1994 | Liotta | 544/317 |
| 5,366,972 A | * 11/1994 | Hargrave et al. | 514/220 |
| 5,444,063 A | 8/1995 | Schinazi | 514/262 |
| 5,684,010 A | 11/1997 | Schinazi | 514/266 |
| 5,767,122 A | 6/1998 | Chu et al. | 514/262 |
| 5,792,773 A | 8/1998 | Chu et al. | 514/274 |
| 5,830,898 A | 11/1998 | Schinazi et al. | 514/262 |
| 5,834,474 A | * 11/1998 | Schinazi | 514/262 |
| 5,925,643 A | 7/1999 | Chu | 514/262 |

FOREIGN PATENT DOCUMENTS

| | | |
|---|---|---|
| AU | 631 786 | 10/1989 |
| WO | WO 92/10497 | 6/1992 |

OTHER PUBLICATIONS

Gulnik et al, Biochemistry, vol. 34, pp. 9282–9287.*
Chu et al, J. Org. Chem, vol. 56, pp. 6503–6505, 1991.*
Chen, Huachun et al. "Pharmacokinetics of (–)–β–D–2–Aminopurine Dioxolane and (–)–β–D–2–Amino –6–Chloropurine Dioxolane and Their Antiviral Metabolite (–)–β–D–Dioxolane Guanine in Rhesus Monkeys" *Antimicrobial Agents and Chemotherapy*, 40, 2332–2336 (1996).

Chen, Huachun et al. "Pharmacokinetics of (–)–β–D–Dioxolane Guanine and Prodrug (–)–βD– 2,6–Diaminopurine Dioxolane Following Intravenous Administration to Rats" manuscript submitted to *Antimicrobial Agents & Chemotherapy*.

Chen, Huachun et al. "Pharmacokintecs of (–)–β–D–2, 6–Diaminopurine Dioxolane and its Metabolite (–)–β–D–Dioxolane Guanine in Rhesus Monkeys" (Draft manuscript).

Good, Steven S et al. "Disposition in the Dog and the Rat of 2,6–Diamino–9–(2–Hydroxyethoxymethyl)Purine(A134U), a Potential Prodrug of Acyclovir" *The Journal of Pharmacology and Experimental Therapeutics* 227, 644–651, USA.

Gu, Z. et al. "Mechanism of Action and In Vitro Activity of 1',3'–Dioxolanylpurine Nucleoside Analogues against Sensitive and Drug–Resistant Human Immunodeficiency Virus Type 1 Variants," *Antimicrobial Agents and Chemotherapy*, 43, 2376–2382 (1999).

Kim, H. O., et al., "Asymmetric Synthesis of 1,3–Dioxolane–Pyrimidine Nucleosides and Their Anti–HIV Activity", *Journal of Medicinal Chemistry*, 1992, vol. 35, No. 11, pp. 1987–1992.

Kim, Hea O. et al. "1,3–Dioxolanylpurine Nucleosides (2R,4R) and (2R,4S) with Selective Anti–HIV–1 Activity in Human Lymphocytes" *Journal of Medicinal Chemistry* 36, 30–37.

Kim, Hea O. et al. "L–β–(2S–4S)– and L–α–(2S,4R)–Dioxolanyl Nucleosides as Potential Anti–HIV Agents: Asymmetric Synthesis and Structure–Activity Relationships" *Journal of Medicinal Chemistry* 36, 519–528.

Kim, Hea O. et al. Potent Anti–HIV and Anti–HBV Activities of (–)–L–β–Dioxolane–C and (+)–L–β–Dioxolane–T and Their Asymmetric Syntheses. *Tetrahedron Letters*, vol. 33, No. 46, pp. 6899–6902, 1992.

(Continued)

*Primary Examiner*—Russell Travers
(74) *Attorney, Agent, or Firm*—Millen, White, Zelano, Branigan, P.C.

(57) ABSTRACT

In accordance with the present invention there is provided a pharmaceutical combination useful for the treatment of viral infections comprising a at least one antiviral active compound of formula (1):

and at least one further therapeutic agent chosen from nucleoside analogues; NNRTIs; and protease inhibitors.

48 Claims, 2 Drawing Sheets

OTHER PUBLICATIONS

Norbeck, Daniel W. et al. "(±)-1-[(2β,4β)-2-(Hydroxymethyl)-4-dioxolanyl]thymine) A new 2',3'-Dideoxynucleoside Prototype with In Vitro Activity Against HIV" Tetrahedron Letters, 30, 6263–6266 (1989).

Schinazi, R. F. et al. "Developmenty of (–)-β-D-2,6-Diaminopurine Dioxolane as a Potential Antiviral Agent", *Antiviral Research*, vol. 23, Supplement 1 (1994).

Spector, Thomas et al. "Conversion of 2,6-Diamino-9-(2-Hydroxyethoxymethyl) Purine to Acyclovir as Catalyzed by Adenosine Deaminase" *Biochemical Pharmacology* vol. 32. No. 17, pp. 2505 2509, 1983 Great Britian.

Triangle Pharmaceuticals, website, "DAPD: A Potential Antiviral Purine Nucleoside Analogue," site last updated on Feb. 5, 1999.

Gulnik et al., Biochemistry, vol. 34, pp. 9282–9287.

* cited by examiner

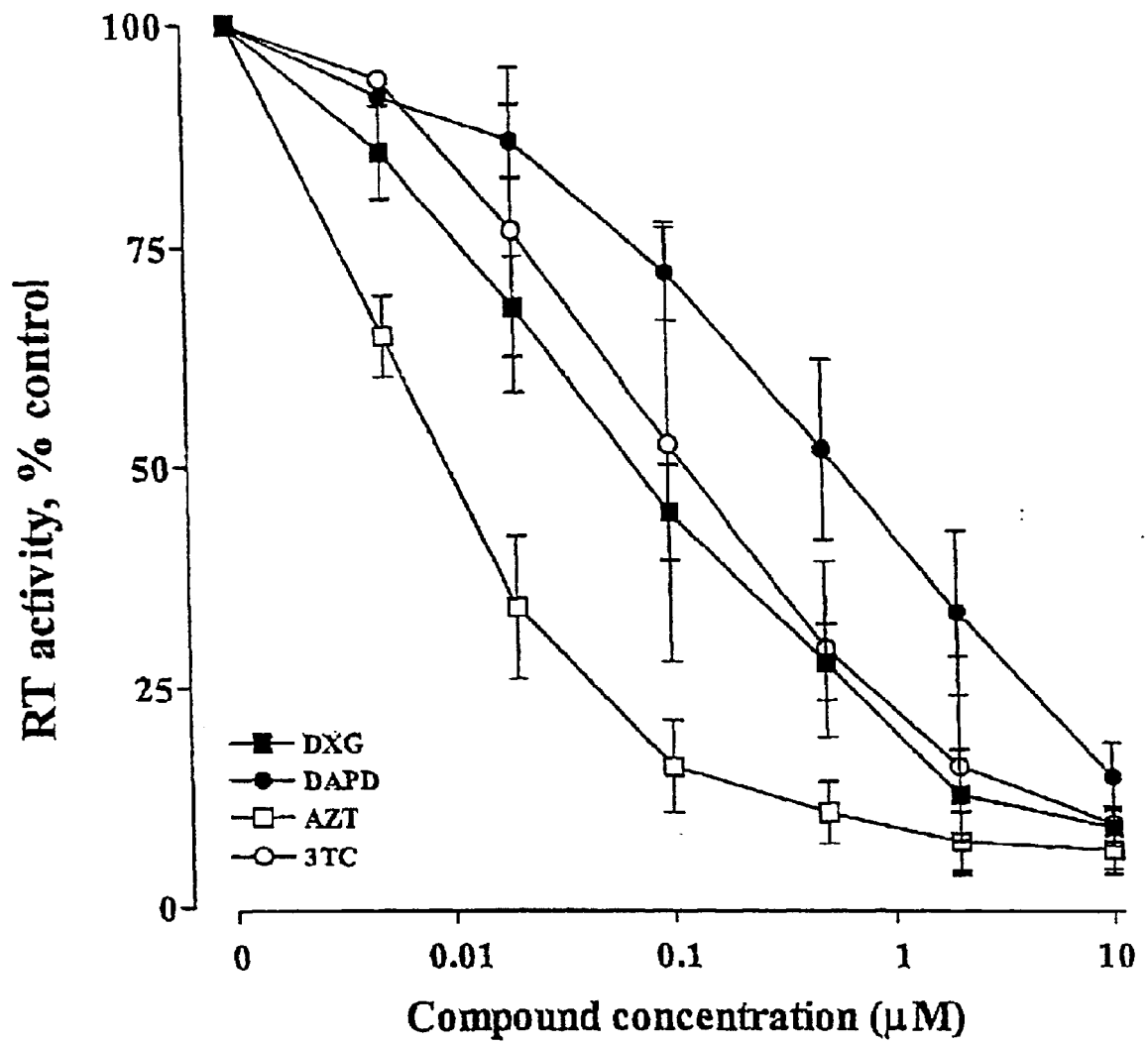
Fig. 1 Dose response curve of inhibition of HIV-1 replication.

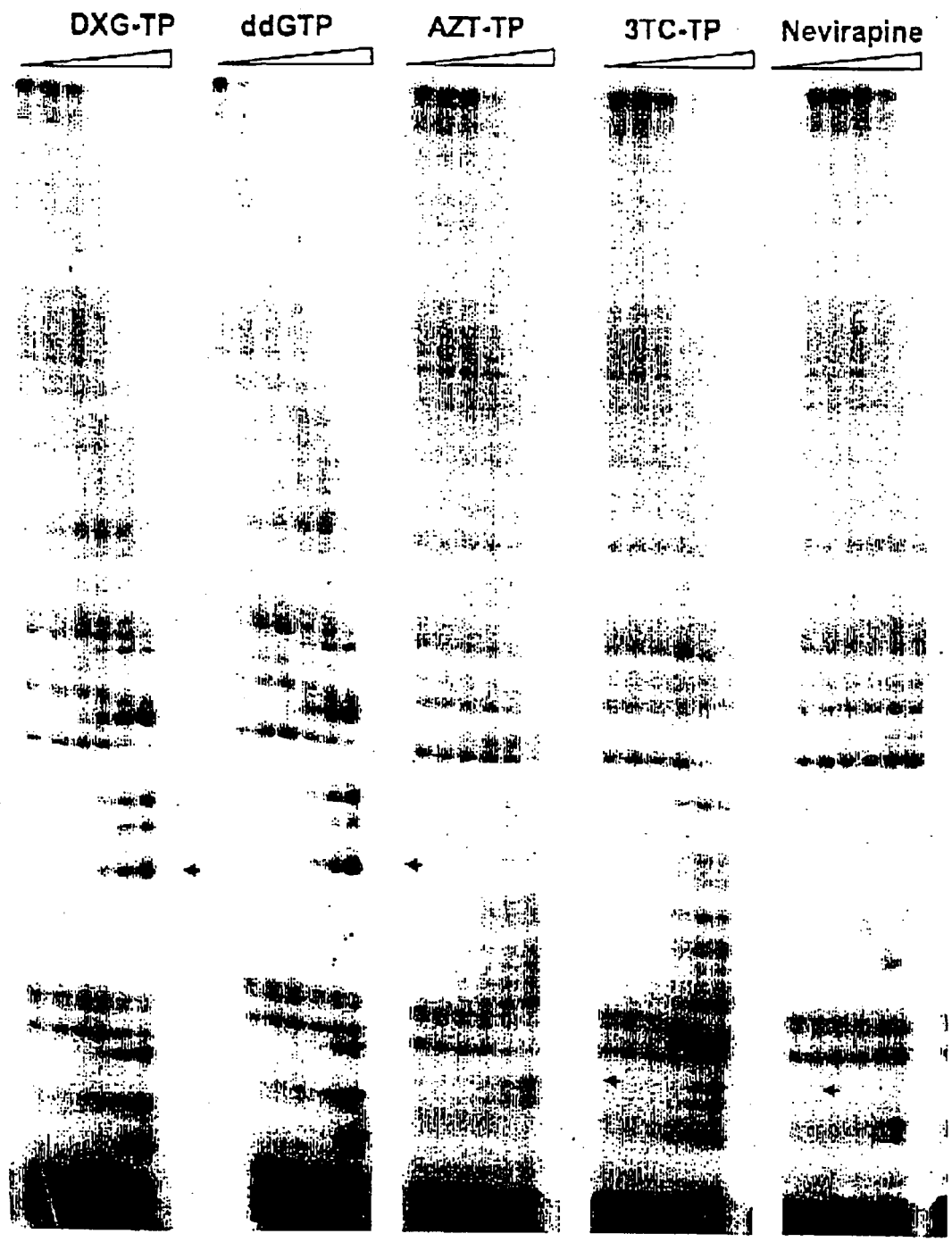
FIG. 2. Comparison of chain-termination effect of DXG-TP with other dideoxynucleotide triphosphates and NNRTI on reverse transcription

PHARMACEUTICAL COMBINATION OF ANTIVIRAL AGENTS

This application claims priority from U.S. 60/122,480 filed Mar. 1, 1999 which is herein incorporated by reference

FIELD OF THE INVENTION

The present invention relates to pharmaceutical combinations useful as antiviral agents. Particularly, the combinations of invention relate to dioxolane nucleosides with at least one further therapeutic agent chosen from nucleoside analogues; NNRTIs; and protease inhibitors.

BACKGROUND OF THE INVENTION

In the United States, more than 12 million new cases of sexually transmitted diseases (STDs) occure each year. Of the top 10 reportable diseases in the United States, five are STDs including chlamydia, gonorrhea, syphilis, the Acquired Immune Deficiency Syndrome (AIDS) and hepatitis B virus (HBV) infection of which AIDS and HBV infection have no cures.

In the case of AIDS, the World Health Organization predicts that by the year 2000 there will be 40 million people worldwide infected with the human immunodeficiency virus (HIV), the virus that causes (AIDS). Hepatitis infections affect 5 times more people that HIV. It has been reported by the World Health Organization that 2000 million people alive today are infected with HBV virus, of whom 350 million are chronically infected and therefore at risk of death from liver disease.

Although mortality rates from AIDS are dropping due to new therapies, AIDS remains the second leading cause of death in adults between the ages of 29 and 40. Combination anti-HIV therapy is now the standard of care for people with HIV. There are now 11 anti-HIV drugs available by prescription. These anti-HIV drugs fall into three categories: nucleosides analogs, which include zidovudine, didanosine, zalcitabine, stavudine and lamivudine; protease inhibitors which include indinavir, nelfinavir, saquinavir and ritonavir and non-nucleoside reverse transcriptase inhibitors (NNRTI) which include nevirapine, delavirdine and efavirenz. Compared to HIV, there is presently only two licensed therapy for chronic hepatitis B virus infection which are interferon and lamivudine. Other drugs are currently under clinical trials including lamivudine, famciclovir, lobucavir and adefovir. But many studies have shown that most patients relapse after completion of therapy and develop resistance to the drugs.

Development of resistance has recently become a major concern in the treatment of HIV and HBV infections. Resistance usually occurs when the drugs being used are not potent enough to completely stop virus replication. If the virus can reproduce at all in the presence of drugs, it has the opportunity to make changes in its structure, called mutations, until it finds one that allows it to reproduce in spite of the drugs. Once a mutation occurs, it then grows unchecked and soon is the dominant strain of the virus in the individual. The drug becomes progressively weaker against the new strain. There is also increasing concern about cross-resistance. Cross-resistance occurs when mutations causing resistance to one drug also cause resistance to another. Several studies have proven that combining two drugs delays the development of resistance to one or both drugs compared to when either drug is used alone. Other studies suggest that three-drug combinations extend this benefit even further. As a result, many people believe that the best way of preventing, or at least delaying resistance is to use multi-drug combination therapies. But as the number of drugs increases, so does the risk or drug interactions and toxicity.

(−)-β-D-2,6-diaminopurine dioxolane (DAPD) and (−)-β-D-1,3-dioxolane guanine (DXG) have been reported to be highly efficacious against HIV-1 in various cell systems, have minimal cross resistance with lamivudine, and low cellular toxicity. Combinations of DAPD and DXG with other therapeutic agents which exhibit potent therapeutic. activity against HIV and HBV would greatly aid in the development of new combination therapy against HIV and HBV.

SUMMARY OF THE INVENTION

In one aspect, the present invention provides a novel pharmaceutical combination useful for the treatment of viral infections comprising a at least one antiviral active compound of formula (1):

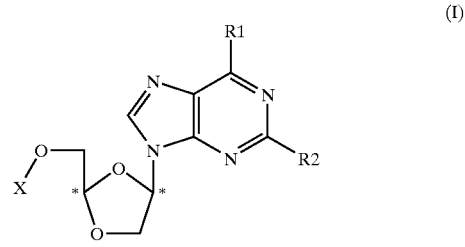

and pharmaceutically acceptable salts thereof,
wherein:
where R1 is chosen from O and the formula —NR$_3$R$_4$ wherein:
  R$_3$ is a saturated or unsaturated C$_{3-8}$ carbocyclic ring optionally substituted with COOH, CONH$_2$, OH, SH, NH$_2$, NO$_2$, C$_{1-6}$ alkyl, C$_{2-6}$ alkenyl, C$_{2-6}$ alkynyl, halogen, COR$_a$ wherein R$_a$ is a C$_{1-6}$ alkyl, C$_{2-6}$ alkenyl, C$_{2-6}$ alkynyl and COOR$_b$ wherein R$_b$ is a C$_{1-6}$ alkyl, C$_{2-6}$ alkenyl, C$_{2-6}$ alkynyl;
  R$_4$ is H or a C$_{1-6}$ alkyl, C$_{2-6}$ alkenyl, C$_{2-6}$ alkynyl;
  R$_3$R$_4$ can also be connected to the nitrogen atom to form a saturated or unsaturated C$_{3-8}$ heterocyclic ring optionally substituted with COOH, CONH2, OH, SH, NH$_2$, N$_2$, C$_{1-6}$ alkyl, C$_{2-5}$ alkenyl, C$_{2-6}$ alkynyl, halogen, COR$_a$ wherein R$_a$ is a C$_{1-6}$ alkyl, C$_{2-5}$ alkenyl, C$_{2-6}$ alkynyl and COOR$_b$ wherein R$_b$ is a C$_{1-6}$ alkyl, C$_{2-6}$ alkenyl, C$_{2-6}$ alkynyl;
R2 is chosen from H, halogen and NH$_2$.
X is chosen from H, monophosphate, diphosphate, triphosphate, carbonyl substituted with a C$_{1-6}$ alkyl, C$_{2-6}$ alkenyl, C$_{2-6}$ alkynyl, C$_{6-10}$ aryl and

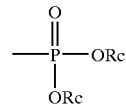

wherein each Rc is independently chosen from H, C$_{1-6}$ alkyl, C$_{2-6}$ alkenyl, C$_{2-6}$ alkynyl and an hydroxy protecting group;

wherein said nucleoside is present in the form of the (−) enantiomer, (+) enantiomer and mixtures thereof, including racemic mixtures;

and at least one further therapeutic agent chosen from nucleoside analogues; NNRTIs(non nucleoside reverse transcriptase inhibitors); and protease inhibitors.

The pharmaceutical combinations of the present invention are useful in therapy, in particular as antivirals.

In another aspect, there is provided a method of treating viral infections in a subject in need of such treatment comprising administering to the subject a therapeutically effective amount of a compound or composition of the invention.

In another aspect, there is provided a pharmaceutical formulation comprising the compound of the invention in combination with a pharmaceutically acceptable carrier or excipient.

In another aspect of the invention is the use of a compound according to formula I, for the manufacture of a medicament for the treatment of viral infections.

BRIEF DESCRIPTION OF THE FIGURES

FIG. 1 represents the dose response curve of inhibition of HIV-1 replication. MT-2 cells were infected with HIV-1IIIB at an MOI of 0.005. The infected cells were cultured in the presence of various concentrations of antiviral compound as shown in this Fig. Viral susceptibility to the compounds was assayed by measurement of HIV-1 RT activity in the culture supernatants as described in Methods. Data are expressed as means±standard deviations for at least five separated experiments, each performed in duplicate.

FIG. 2 represents the comparison of chain-termination effect of DXG-TP with other dideoxynuclectide triphosphates and NNRTI on reverse transcription. The bands at the top of the gel were full-length cDNA products in this assay. The solid arrows show examples of chain termination bands generated by each of the dideoxynucleotide inhibitors.

DETAILED DESCRIPTION OF THE INVENTION

In one embodiment, compounds of the present invention comprise those wherein the following embodiments are present, either independently or in combination.

In one aspect, the present invention provides a novel pharmaceutical combination useful for the treatment of viral infections comprising a at least one antiviral active compound of formula (1):

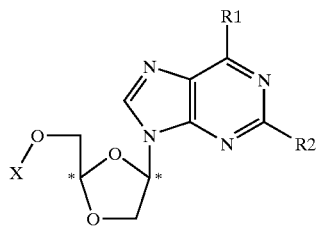

and pharmaceutically acceptable salts thereof, wherein:

R1 is chosen from O and the formula —NR$_3$R$_4$ wherein:
R$_3$ is a saturated or unsaturated C$_{3-9}$ carbocyclic ring optionally substituted with COOH, CONH$_2$, OH, SH, NH$_2$, NO$_2$, C$_{1-6}$ alkyl, C$_{2-6}$ alkenyl, C$_{2-6}$ alkynyl, halogen, COR$_a$ wherein R$_a$ is a C$_{1-6}$ alkyl, C$_{2-6}$ alkenyl, C$_{2-6}$ alkynyl and COOR$_b$ wherein R$_b$ is a C$_{1-6}$ alkyl, C$_{2-6}$ alkenyl, C$_{2-6}$ alkynyl;

R$_4$ is H or a C$_{1-6}$ alkyl, C$_{2-6}$ alkenyl, C$_{2-6}$ alkynyl;

R$_3$R$_4$ can also be connected to the nitrogen atom to form a saturated or unsaturated C$_{3-8}$ heterocyclic ring optionally substituted with COOH, CONH2, OH, SH, NH$_2$, NO$_2$, C$_{1-6}$ alkyl, C$_{2-6}$ alkenyl, C$_{2-6}$ alkynyl, halogen, COR$_a$ wherein R$_a$ is a C$_{1-6}$ alkyl, C$_{2-6}$ alkenyl, C$_{2-6}$ alkynyl and COOR$_b$ wherein R$_b$ is C$_{2-6}$ alkyl, C$_{2-6}$ alkenyl, C$_{2-6}$ alkynyl;

R2 is chosen from H, halogen and NH$_2$.

X is chosen from H, monophosphate, diphosphate, triphosphate, carbonyl substituted with a C$_{1-6}$ alkyl, C$_{2-6}$ alkenyl, C$_{2-6}$ alkynyl, C$_{5-10}$ aryl and

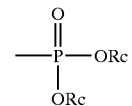

wherein each Rc is independently chosen from H, C$_{1-6}$ alkyl, C$_{2-6}$ alkenyl, C$_{2-6}$ alkynyl and an hydroxy protecting group;

wherein said nucleoside is present in the form of the (−) enantiomer, (+) enantiomer and mixtures thereof, including racemic mixtures;

and at least one further therapeutic agent chosen from nucleoside analogues; NNRTIs; and protease inhibitors.

In one embodiment, X is chosen from H, monophosphate, diphosphate and triphosphate.

In one embodiment, X is H.

Alternatively X is

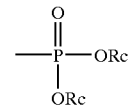

wherein each Rc are independently chosen from phosphate, diphosphate H, C$_{1-6}$ alkyl, C$_{2-6}$ alkenyl, C$_{2-6}$ alkynyl and an hydroxy protecting group chosen from S-acylthioethyl ester, acyloxymethyl ester and alkyl methyl carbonate.

In one embodiment, X is

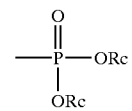

wherein each Rc are independently an hydroxy protecting group chosen from acetyl-2-thioethyl ester, pivaloyloxymethyl ester and isopropyloxycarbonyloxymethyl ester.

In one embodiment, R1 is represented by NH$_2$ or O

In a further embodiment, R$_3$ is H or methyl.

In a further embodiment, R$_3$ is H.

In a further embodiment R$_4$ is chosen from H, COOH, CONH$_2$, C$_{1,6}$ alkyl, C$_{2,6}$ alkenyl, C$_{2-6}$ alkynyl and COOR$_b$ wherein R$_b$ is a C$_{1-6}$ alkyl, C$_{2-6}$ alkenyl, C$_{2-6}$ alkynyl.

In a further embodiment R$_4$ is H, COOH, or C$_{1-6}$ alkyl.

In a further embodiment R$_4$ is H, COOH, methyl or ethyl.

In a further embodiment R$_4$ is methyl or ethyl.

In an alternative embodiment, R$_4$ is COOH.

In a further embodiment R$_4$ is H.

In a further embodiment, $R_3$ is H or methyl and $R_4$ is H.

In a further embodiment $R_4$ and $R_3$ are H.

In one embodiment, R2 is chosen from H, halogen and $NH_2$.

In a further embodiment, R2 is Cl or $NH_2$.

In one embodiment, R2 is $NH_2$.

In one embodiment, the pharmaceutical combinations of this invention may contain at least one other antiviral agent chosen from 3TC (lamivudine), AZT (zidovudine), FTC (5-fluoro-1-[2-(hydroxymethyl)-1,3-oxathiolan-5-yl] cytosine), d4T (2',3'-dideoxy-2',3'-didehydro-thymidine, stavudine and Zerit), nevirapine, DMP-226, nelfinavir, delavirdine, 9-[(2-hydroxymethyl)-1,3-dioxolan-4-yl] guanine, 2-amino-9-[(2-hydroxymethyl)-1,3-dioxolan-4-yl] adenine, MKC-442, 1592U89 (abacavir), 141W94, MK-639, BMS-234475, PNU-140690, ABT-378, DMP-450, Indinavir, saquinavir, ritonavir, efavirenz (sustiva), TIBO, HEPT, BEAP, α-APA, TSAO, calanolides, L-697,661, 2',3'-dideoxycytidine (ddC or zalcitabine), 2',3'-dideoxyadenosine, 2',3'-dideoxyinosine (ddI or didanosine), 3'-deoxythymidine and 2',3'-dideoxy-2',3'-didehydrocytidine and ribavirin; acyclic nucleosides such as acyclovir, ganciclovir, interferons such as alpha-, beta- and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease-such as L-735,524.

In one embodiment, the pharmaceutical combinations of the present invention may contain at least one other antiviral agent chosen from zidovudine, didanosine, zalcitabine, stavudine, lamivudine, nevirapine, delavirdine, efavirenz, indinavir, nelfinavir, saquinavir and ritonavir.

In one embodiment, the pharmaceutical combinations of the present invention may contain at least one other antiviral agent chosen from chosen from zidovudine, lamivudine and nevirapine.

In one embodiment, the compounds of the invention are employed together with zidovudine, stavudine, or lamivudine.

In one embodiment, the compounds of the invention may be employed together with zidovudine.

In one embodiment, the compounds of the invention may be employed together with stavudine.

In one embodiment, the compounds of the invention may be employed together with lamivudine.

In one embodiment, the compounds of the invention may be employed together with nevirapine.

In one embodiment, the compounds of the invention may be employed together efavirenz The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

In one embodiment, the pharmaceutical combination of the present invention include a compound of formula (Ia) and (1b):

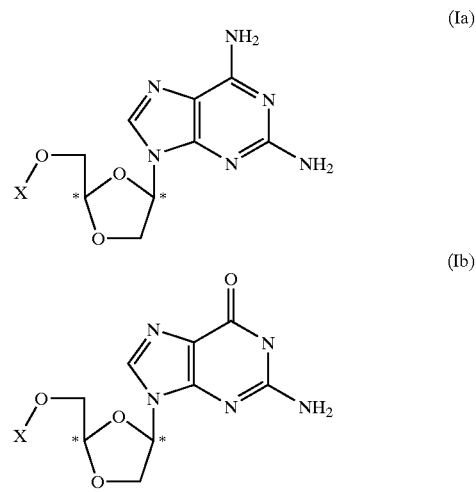

In one embodiment, X is chosen from H, monophosphate, diphosphate and triphosphate.

X is most preferably H.

Alternatively X is

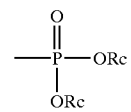

wherein each Rc are independently chosen from H, $C_{1-6}$ alkyl, $C_{2-6}$ alkenyl, $C_{2-6}$ alkynyl and an hydroxy protecting group chosen from S-acylthioethyl ester, acyloxymethyl ester and alkyl methyl carbonate.

In one embodiment, X is

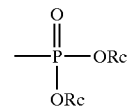

wherein each Rc are independently an hydroxy protecting group chosen from acetyl-2-thioethyl ester, pivaloyloxymethyl ester and isopropyloxycarbonyloxymethyl ester.

It will be appreciated by those skilled in the art that the compounds of formula (I), (Ia) and (1b) contain at least two chiral centres which are marked by an asterisk (*) on the general formula (I) and (Ia). The compounds of formula (I) and (Ia) thus exist in the form of two different optical isomers (i.e. (+) or (−) enantiomers or β-L and β-D). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In one embodiment, the pharmaceutical combination of the present invention include the one of the following compounds:

Compound A (−)-β-D-2,6-diaminopurine-1,3-dioxolane (DAPD)

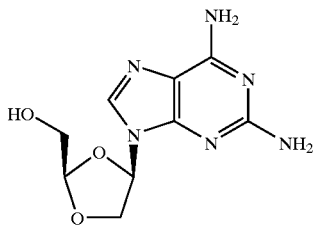

Compound B (−)-β-D-1,3-dioxolane guanine (DXG)

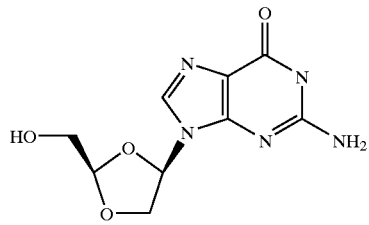

In one embodiment, the compounds formula (1) (1a) and (1b) present in the pharmaceutical combination of the present invention are provided in the form of a single enantiomer at least 95%, more preferably at least 97% and most preferably at least 99% free of the corresponding enantiomer.

In one embodiment, the compounds formula (1), (1a) and (1b) present in the pharmaceutical combination of the present invention are in the form of the (+) enantiomer at least 95% free of the corresponding (−) enantiomer.

In one embodiment, the compounds formula (1), (1a) and (1b) present in the pharmaceutical combination of the present invention are in the form of the (+) enantiomer at least 97% free of the corresponding (−) enantiomer.

In one embodiment, the compounds formula (1), (1a) and (1b) present in the pharmaceutical combination of the present invention are in the form of the (+) enantiomer at least 99% free of the corresponding (−) enantiomer. In a further embodiment, the compounds formula (1), (1a) and (1b) present in the pharmaceutical combination of the present invention are in the form of the (−) enantiomer at least 95% free of the corresponding (+) enantiomer.

In one embodiment, the compounds formula (1), (1a) and (1b) present in the pharmaceutical combination of the present invention are in the form of the (−) enantiomer at least 97% free of the corresponding (+) enantiomer.

In one embodiment, the compounds formula (1), (1a) and (1b) present in the pharmaceutical combination of the present invention are in the form of the (−) enantiomer at least 99% free of the corresponding (+) enantiomer.

In one embodiment, the compound of formula (1), (1a) and (1b) present in the pharmaceutical combination of the present invention is chosen from Compound A and Compound B In one embodiment, the compound of formula (1), (1a) and (1b) present in the pharmaceutical combination of the present invention is Compound A.

In one embodiment, the pharmaceutical combination of the present invention comprises at least one therapeutic agent is chosen from Compound A and Compound B and at least one additional therapeutic agent is chosen from zidovudine, didanosine, zalcitabine, stavudine, lamivudine, nevirapine, delavirdine, efavirenz, indinavir, nelfinavir, saquinavir and ritonavir.

In one embodiment, the pharmaceutical combination of the present invention is a synergistic combination of therapeutic agents comprising Compound A or Compound B and at least one additional therapeutic agent chosen from zidovudine, lamivudine and nevirapine.

There is also provided a pharmaceutically acceptable salts of the compounds formula (1), (1a) and (1b) present in the pharmaceutical combination of the present invention. By the term pharmaceutically acceptable salts of compounds of general formula (1), (1a) and (1b) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

References hereinafter to the pharmaceutical combination according to the invention includes compounds of the general formula (1), (1a) and (1b) and there pharmaceutically acceptable salts.

All references cited in the present application are incorporated by reference.

By the term "heterocyclic ring" is meant a substituted (e.g. by a $C_{1-6}$ alkyl, halogen, amino, or $NO_2$) or unsubstituted, saturated or unsaturated, $C_{3-8}$ cycloalkyl, wherein said cycloakyl is interrupted by at least one heteroatom, e.g. oxygen, sulfur or nitrogen. Example of heterocyclic rings include but are not limited to epoxide; furane; oxathiolane; dithiolane; dioxolane; pyrrole; pyrrolidine; imidazole; pyridine; pyrimidine; indole; piperidine; morpholine; and thiomorpholine.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

When there is a sulfur atom present, the sulfur atom can be at different oxydation level, S, SO, or $SO_2$. All such oxidation level are within the scope of the present invention.

It will be appreciated that the amount of pharmaceutical combination according to the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 500 mg/kg/day, most preferably in the range of 1 to 300 mg/kg/day.

The desired dose may conveniently be presented in a single dose or as divided dose administered at appropriate intervals, for example as two, three, four or more doses per day.

The compounds of formula (1), (1a) and (1b) present in the pharmaceutical combination of the present invention are either additive or synergistic with the additional therapeutic agents in the combination and/or remove the cytotoxic effects of the other components.

The pharmaceutical combination according to the present invention is conveniently administered in unit dosage form; for example containing 10 to 1500 mg, conveniently 20 to 1000 mg, most conveniently 50 to 300 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) and (Ia) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The advantageous effects of the combination of the compounds of formula (1), (1a) arid/or (1b) and the additional therapeutic agents are realized over a wide ratio. For example 1:250 to 250:1.

In one embodiment, the ratio of the compounds of formula (1), (1a) and/or (1b) to the additional therapeutic agents in the present invention is between 1:50 to 50:1.

In one embodiment, the ratio of the compounds of formula (1), (1a) and/or (1b) to the additional therapeutic agents in our invention is between 1:20 to 20:1.

In a further embodiment, one may use from about 1:1 to about 1:15 of compounds of the invention second therapeutic agent. In a further embodiment, one may use from about 1:1 to about 1:10 of compounds of the invention:second therapeutic agent. In a further embodiment, one may use from about 1:1 to about 1:5 of compounds of the invention:second therapeutic agent. In a further embodiment, one may use from about 1:1 to about 1:3 of compounds of the invention:second therapeutic agent. If a further therapeutic agent is added, ratios will be adjusted accordingly.

While it is possible that, for use in therapy, a compound of the invention may be administered as the raw chemical it is preferable to present the active ingredient as a pharmaceutical formulation. The invention thus further provides a pharmaceutical formulation comprising a compound of formula (1), (1a) and (1b) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous). administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical combination according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the pharmaceutical combination according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredients in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compounds with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the pharmaceutical combination according to the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the pharmaceutical combination according to the present invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the pharmaceutical combination according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following examples are provided to illustrate various embodiments of the present invention and shall not be considered as limiting in scope.

The Compounds

The compounds DXG, DAPD, DXG 5'-triphosphate (DXG-TP), (+) enantiomer of -D-1',3'-dioxolane guanosine, and lamivudine were synthesized at BioChem Pharma. as previously described (Belleau et al., 1989., Design and activity of a novel lass of nucleoside analogs effective against HIV-1. Internatl. Conference on AIDS, Montreal (Quebec) Canada, June 4–9.; Siddiqui et al., 1993, Bioorg. Med. Chem. Lett. 3:1543–1546). All of the dioxolanyl nucleosides were enantiomerically pure.

Cells and Viruses

Human cord blood mononuclear cells (CBMCs) and peripheral blood mononuclear cells (PBMC) were obtained from HIV-1 negative and hepatitis B virus negative donors (Department of Obstetrics, Jewish General Hospital, Montreal) and were isolated using Ficoll-Hypaque (Pharmacia) density gradient centrifugation. The CBMCs were then cultured under stimulation with 0.1% (v/v) (5 mg/ml) Phytohemagglutinin (PHA; Boehringer Mannheim, Montreal Canada) in RPMI-1640 medium (Gibco BRL Laboratories, Mississauga, Canada) containing 10% fetal calf serum (Flow Laboratories, Toronto, Canada), 2 mM glutamine, 100 U of penicillin, 100 mg of streptomycin and 15 U interleukin 2 (IL-2, Boehringer Mannheim) per ml at 37° C. and 5% $CO_2$ for 3–4 days before used for antiviral assays (Rooke et al, 1990, Virol. 176:205–215).

T-cell lines, i.e. MT-2, MT-4, H9 and Jurkat, and a monocyte cell line, i.e. U937, were obtained from either NIH AIDS Research and Reference Reagents (MD) or ATCC. These cells were used for antiviral and cytotoxicity studies and maintained as suspension cultures in RPMI-1640 medium containing 10% fetal calf serum, 2 mM glutamine, 100 U of penicillin, and 100 mg of streptomycin per ml. Other tumor cell lines, including Molt-4, HT-1080, DU145 and HepG2 obtained from ATCC,and one normal cell line (human skin fibroblasts, HSF) obtained from Dr. M. Chrevette, (McGill University, Montreal, Canada), were also used for cytotoxicity assays and cultured in RPMI-1640 medium.

HIV-1$_{IIIB}$ laboratory strain and HXB2-D recombinant of HIV-1 were kindly supplied by R. C. Gallo (Institute of Human Virology, Baltimore, Md.). Recombinant mutated HIV-1 variants were prepared by site-directed mutagenesis as previously described (Gu et al., 1992. J. Virol. 66:12–19. and Gu, et al 1994,. Antimicrob. Agents Chemother. 38:275–281.). The recombinant viruses were generated by transfection of proviral DNA into MT-4 cells with Lipofectamine using the protocol recommended by the manufacturer .(Gibco BRL, Montreal, Canada). HIV-1 clinical isolates were obtained by coculture of peripheral blood lymphocytes from HIV-1 infected individuals with the CBMCs, and then propagated on CBMCs in the absence of drugs as described by Salomon et al. (1994, J. Clin. microbial. 32:2000–2002). Stock viruses were prepared from clarified culture supernatants by centrifugation and stored at −70° C. The viruses were titrated by limited dilution with a 4-fold serial dilution.

Antiviral Assays

Anti-HIV-1 activities of DXG and its prodrug DAPD were assessed by employing different HIV-1 variants and types of cells. Most experiments were performed with a laboratory strain HIV-1$_{III}$. A number of recombinant drug-resistance variants, and low passage clinical isolates from individuals who had received long-term anti-HIV therapy were also used to evaluate the effects of these two compounds. The methods used to assess the antiviral effect of the compounds have been previously described (Gu et al., 1992, J. Virol. 66:12–19, and Gu, et al 1994,. Antimicrob. Agents Chemother. 38:275–281,. Rando et al., 1995; J. Biol. Chem. 270:1754–1760, Salomon et al, 1994, J. Clin. Microbiol. 32:2000–2002). The cells were incubated with virus using the indicated multiplicity of infection (MOI) for 2–3 hrs. The MOI used for each experiment was dependent upon the cell line and virus strain used, and was generally in the range of 0.005 to 0.5. For example, in assays performed using the established cell line MT-2, HIV-1$_{IIIB}$ at an MOI of 0.005 was used to infect cells. The unbound virus was then removed by washing the cells, followed by plating the cells into a 96-well plate. The infected cells were cultured in the presence of a serial concentrations of the test compound for 5–7 days. The anti-HIV-1 efficacy was determined by testing for HIV-1 RT activity in the cell culture supernatants. All assays were performed in duplicate and at least two independent experiments were performed. Anti-HIV-1 efficacy of DXG and DAPD was compared to the approved anti-HIV-1 drugs AZT and/or lamivudine controls in each individual experiment. The susceptibilities of the HIV-1 variants to antiretroviral agents are expressed as the mean of the $EC_{50}$ determinations.

Combination effects between DXG and approved anti-HIV-1 agents were assessed in CBMCs using HIV-1$_{IIIB}$. The combinations of the inhibitors was performed with a checker board cross. The antiviral effects were monitored through testing RT activity in the culture supernatants at day 7. The data was analyzed according to the method described by Chou and Talalay (Chou and Talalay, 1984, Adv. Enzyme Regul. 22:27–55). The combination indexes (CIs) of DXG with other anti-HIV-1 agents were calculated by using CalcuSyn program (Biosoft, Cambridge, UK). Theoretically, CI of 1 indicates additive effect; CIs of >1 and <1 stand for antagonism and synergism between the drugs combined, respectively.

Cytotoxicity Analysis

The cellular toxicity of the BCH compounds were assessed on various cells using [$^3$H]-thymidine uptake. The various cells, including Molt-4, HT1080, DU-145, HepG 2 and HSF, were plated at a concentration of 1–2×10$^3$ cells per well (96 well plates). However, PHA-stimulated PBMCs were cultured at a concentration of 4×10$^4$. After a 24 hr incubation period, 10-fold serial diluted compounds (10$^{-4}$ M to 10$^{-10}$ M) were added to the culture medium and the cells were further incubated for 72 hrs. [$^3$H]-thymidine was added during the final 18 hr incubation period. After incubation with the [$^3$H]-thymidine, the cells were washed once with PBS, treated with trypsin it the cells were adherent, and then resuspended in water (hypotonic lysing of cells) The cellular extract was applied directly to a Tomtec Harvester 96. Using this instrument the extracted DNA is adsorbed onto filters, washed and the incorporated [$^3$H]-thymidine is then counted. The 50% cytotoxic concentration (CC$_{50}$) was determined by comparing the radioactive counts per minute of the samples in the presence of the compounds against the control.

The cellular toxicity of the compounds was also tested by WST-1 staining through assessing proliferation of MT-2, H9, Jurkat, U937, and CBMCs. The established cell lines were cultured in RPMI medium in 96-well plates at a density of 5×10$^4$ cells/well while CBMCs were plated at a concentration of 0.5×10$^6$/well. A 10-fold serial diluted (10$^{-4}$–10$^{-7}$ M) compound was added at day zero. At day 4, the cells were passaged by changing half medium containing appropriately diluted compound. The cell activities were assessed at day 7 using the WST-1 reagent (Boehringer Mannheim) following the protocol provided by the supplier.

Reverse Transcriptase Enzyme Assays

Wild type (wt) version of recombinant HIV-1 RT were expressed with a histidine tag in an *E. coli* protein expression system. The enzymes was purified up to 95% homogeneity as described by Gu et al.(1994,. J. Biol. Chem. 269:28118–28122., and 1995, Proc. Natl. Acad. Sci. USA 92:2760–2764.).

RT inhibition assay. The inhibition of HIV-1 RT RNA dependent DNA polymerase activity of DXG-TP was assessed under steady-state enzymatic kinetics by employing homopolymeric RNA templates/DNA primers (T/P) and a heteropolymeric RNA template/DNA primer. The heteropolymeric RNA template contains the HIV-1 primer binding sequence, U5 and R regions (designated as HIV-PBS). The HIV-PBS RNA was in vitro transcribed from a plasmid DNA as described previously (Gu et al., 1994,. J. Biol. Chem. 269:28118–28122.). The oligodeoxynucleotide primer (dPR) is an 18-mer (5'-GTCCCTGTTCGGGCGCCA-3') which is complementary to the HIV-1 primer binding sequence. The complex of HIV-PBS and dPR T/P was prepared by mixing a 1:2 ratio in 50 mM Tris-HCl (pH 7.8) containing 60 mM KCl, heating to 95° C. for 2 min, and then slowly cooling down to room temperature (Gu et al., 1994,. J. Biol. Chem. 269:28118–28122). The reverse transcription reaction contained final concentrations of 50 mM Tris-HCl, pH 7.8, 60 mM KCl, 10 mM MgCl$_2$, 0.1 U/ml homopolymeric T/P and 5 μM [$^3$H]dNTP substrate or 25 nM HIV-PBS/dPR and 5 μM each of dTTP, dCTP, dGTP and [-$^{32}$P]dATP in 100 ml. Reactions were incubated for 30 min at 37° C. in the presence or absence of dideoxynucleoside triphosphate inhibitors as described by Gu et al. (1994,. J. Biol. Chem. 269:28118–28122.). Inhibition of dNTP incorporation/chain termination. The effect of DXG-TP on RT activity was also assessed using the chain termination/dNTP incorporation assay in which inhibition of nascent DNA synthesis (chain termination) was monitored based upon cDNA synthesis as previously described (Arts et al., 1993; J. Biol. Hem. 269:14672–14680 and Gu et al., 1995, Proc. Natl. Acad. Sci. USA 92:2760–2764). HIV-PBS RNA template and dPR DNA primer were used in this system. The RT reactions were performed in 20 ml volumes containing 50 mM Tris (pH 7.8), 75 mM KCl, 10 mM $MgCl_2$, 100 $\mu$M of dNTPs. The HIV-PBS RNA template (50 nM) and [$-^{32}$P]-ATP labeled oligodeoxynucleotide primer (125 nM) were included in the reaction. The mixture was first denatured at 85° C. for 2 minutes, then cooled to 55° C. for 8 min, and finally cooled to 37° C. at which time recombinant HIV RT was added (42.5 nM). The reactions were allowed to proceed at 37° C. for 60 min in the presence or absence of inhibitors. The transcribed DNA products were separated on a 5% denaturing polyacrylamide gel and visualized by exposure to X-ray film.

Determination of HIV-1 RT Genotype

To determine the RT genotype of the HIV-1 clinical isolates, proviral DNA of each isolate was extracted from infected CD4$^+$ T-cells or CBMCs as previously reported (Gu et al., 1992). The complete RT coding regions were amplified by PCR employing a primer pair consisting of the up-stream primer RT01 (5'-GTAGAATTCTGTTGACTCAGATTGG-3'), and the down-stream primer RT02 (5'-GATAAGCTTGGGCCTTATCTATTCCAT-3') as previously described (Gu et al, 1992, J. Virol. 66:12–19.). The amplified fragment were 1.7 kb and contained the complete RT coding sequence. The PCR amplified fragments were separated by agarose gel electrophoresis and purified by Qiaquick Gel Extraction kit (Qiagen, Mississauga, Ontario, Canada). The purified PCR product was directly sequenced using primer RTS (5'-CCAAAAGTTAAACAATGGC-3') which is located at the 5' portion of the RT coding region (nucleotide 2603–2621 of HXB2-D co-ordinates). The nucleic acid sequence of RT was sequenced and compared with the published sequences of wild-type HIV-1 strains.

EXAMPLE 1

Anti-HIV-1 Efficacy of Dioxolanyl Analogues in Various Cells

Since anabolic efficiency of nucleoside analogues, i.e. phosphorylation and prodrug conversion, is mediated by the related cellular enzymes which activities depend on type of cells, we assessed the anti-HIV-1 efficacy of the dioxolanyl compounds, DXG and , in human CBMCs and a variety of human T and monocyte cell lines. All data in these assays were obtained using HIV-1$_{IIIB}$ Approved anti-HIV agents, AZT and lamivudine, were used in each of the experiments as controls. Table 1 summarizes the data of the antiviral efficacy of the compounds while FIG. 1 shows a dose response curve for the inhibition of HIV-1 in, MT-2 cells. Generally, The dioxolanyl compounds had the same efficacy in CBMCs and in T-cell lines. For example, $EC_{50}$S were 0.046 $\mu$M and 0.085 $\mu$M for DXG tested in CBMCs and in MT-2 cells, respectively. $EC_{50}$s for DAPD were usually 5–20-fold higher than those for DXG in various cells, e.g. 0.97 $\mu$M and 0.54 $\mu$M $EC_{50}$s for this prodrug in CBMCs and in MT-2 cells, respectively. In addition, comparing with the anti-HIV-1 efficacy of the approved agents, DXG were generally equivalent to the efficacy of lamivudine in the various cells, but approximately 5–10-fold less than that of AZT (Table 1).

TABLE 1

Inhibitory effects of DXG and DAPD on HIV-1 replication[a]

$EC_{50}$, $\mu$M of mean values ± SD (No. of experiments)

| Cell | DXG | DAPD | lamivudine | AZT |
| --- | --- | --- | --- | --- |
| CBMCs | 0.046 ± 0.017 (3) | 0.97 ± 0.092 (2) | 0.023 ± 0.011 (4) | 0.0051 ± 0.003 (4) |
| MT-2 | 0.085 ± 0.026 (7) | 0.54 ± 0.29 (6) | 0.091 ± 0.08 (6) | 0.0076 ± 0.0044 (5) |
| MT-4 | 0.051 ± 0.009 (2) | 0.94 ± 0.028 (2) | 0.056 ± 0.014 (2) | 0.008 ± 0.005 (2) |
| Jurkat | 0.34 ± 0.14 (2) | 1.37 ± 0.72 (2) | 0.53 ± 0.02 (2) | 0.011 ± 0.007 (2) |
| H9 | 0.06 ± 0.05 (2) | 0.075 ± 0.04 (2) | ND[b] | 0.041 ± 0.05 (2) |
| U937[c] | 0.41 | 1.3 | ND | 0.025 |

[a]All assays were performed using laboratory strain HIV-1$_{IEB}$
[b]ND, not determined
[c]Single experiment in duplicate.

We also compared the antiviral efficacy between (−) and (+) enantiomers of -D-1',3'-dioxolane guanosine. Our results showed that the (+) enantiomer, with 0.7 $\mu$M of $EC_{50}$, had less antiretroviral activity than its (−) enantiomer partner tested in MT-2-cells.

EXAMPLE 2

Susceptibility of Recombinant Drug-resistance HIV-1 Variants to DXG and DAPD

Recombinant HIV-1 variants carrying drug-resistant mutation(s) were employed to test the cross-resistance phenotype of DXG and DAPD in CBMCs and MT-2 cells. Table 2 summarizes the background of the variants and their sensitivities to the dioxolanylpurine compounds as well as the approved NRTIs in CBMCs. These mutants consist of those seen for the commonest RT inhibitor-resistance HIV-1 variants generated either in vitro selection or from patients undergoing anti-retroviral therapy with NRTIs, such as AZT, lamivudine, 2',3'-dideoxyinosine (ddI) and ddC. All of the recombinants are derived from HXB2-D. The data in Table 2 indicated that the variants of HIV-1 carrying ddI-, ddC- or lamivudine-resistance mutations, i.e. 65K, 74V, and 184V substitutions in the RT gene, had minimal (2 to 5-fold) decreased sensitivity to DXG and DAPD referred to the wt HXB2-D. In addition, the variant bearing mutations of 41L and 215Y combined with 184V, which has a high-level resistance to lamivudine but reversed sensitivity to AZT, had approximate 2-fold decreased sensitivity to DXG which was similar to the 184V single mutated recombinant.

In contrast, AZT resistant virus, i.e. the recombinant carrying 41L, 70R, 215Y and 219Q multiple substitutions in the RT, remained completely sensitive to DXG and DAPD both in CBMCs (Table 2), this was also observed in MT-2 cells. In addition, antiviral assays also demonstrated that these dioxolanyl nucleoside analogues were sensitive against NNRTI-resistant and protease inhibitor-resistant variants (Table 2).

wt strains, i.e. HIV-1$_{IIIB}$ and HXB2-D assessed in CBMCs (see Tables 1 and 2).

The isolates 3350 and 4205, from patients who had received lamivudine therapy, carried 184V mutation in their RTs and were high-degree resistance to lamivudine but remained sensitive to AZT. Consistent with the results obtained using the recombinant variants (Table 2), these 184V mutated isolates had an approximate 5-fold decreased susceptibility to DXG and DAPD when compared to the lamivudine and AZT sensitive isolates (Table 3).

TABLE 2

Effect of DXG and DAPD on recombinant drug-resistant HIV-1

| Recombinant HXB2-D[a] | Resistance to: | EC$_{50}$ ($\mu$M) in CBMCs of: | | | |
|---|---|---|---|---|---|
| | | DXG | DAPD | lamivudine | AZT |
| WT | wt | 0.21 ± 0.05 | 1.1 ± 0.16 | 0.041 ± 0.012 | 0.0041 ± 0.001 |
| 65R | ddI, ddC, lamivudine | 1.2 ± 0.2 | 6.5 ± 2.1 | 0.36 ± 0.17 | 0.003 ± 0.0003 |
| 74V | ddI | 1.3 ± 0.8 | 6.6 ± 3.4 | 0.12 ± 0.07 | 0.006 ± 0.0002 |
| 184V | lamivudine, ddI, ddC | 0.44 ± 0.07 | 2.1 ± 0.20 | >50[b] | 0.0027 ± 0.000 |
| 41L/70R/215Y/219Q | AZT | 0.24 ± 0.02 | 1.25 ± 0.59 | 0.062 ± 0.020 | 0.082 ± 0.08 |
| 41L/215Y/184V | lamivudine | 0.41 ± 0.10 | 2.3 ± 0.05 | >50[b] | 0.006 ± 0.004 |
| 106A/181C[c] | NNRTIs | 0.05 ± 0.007 | ND[d] | ND | 0.30 ± 0.005 |
| 10R/46I/63P/82T/84V[e] | saquinavir | 0.12 ± 0.03 | 1.37 ± 0.06 | ND | 0.0032 ± 0.001 |

[a]The recombinant viruses are wild-type (wt) and mutants harboring the substitution(s) in the RT indicated.
[b]The highest concentration of lamivudine used in these assays was 50 $\mu$M.
[c]EC$_{50}$ for nevirapine was >10 $\mu$M.
[d]ND, not determined
[e]Protease genotype; EC$_{50}$ for saquinavir was 0.075 ± 0.011 $\mu$M.

EXAMPLE 3

Susceptibility of HIV-1 Clinical Isolates to DXG and DAPD

The population of HIV-1 in infected individual is quasispecies and the sensitivity of these different viruses found in clinical isolates to antiviral chemotherapy might be quite variable. In addition, HIV-1 isolates obtained from patients receiving long-term antiretroviral therapy might behave differently from cloned virus containing genetically engineered mutations in the RT gene. For these reasons, clinical isolates of HIV-1 from antiviral naive and drug-treated patients were assayed in PHA-stimulated CBMCs for their sensitivity to DXG and DAPD accompanied with approved antiretroviral agents. The genotype of the HIV-1 clinical isolates were determined as described above.

Table 3 shows the summary of the recent therapy history for patients from which the HIV-1 isolates were obtained, the RT genotype of the isolates, and their sensitivity to the indicated anti-HIV agents. Four isolates, i.e. number 3887, 4246, 4877 and 4526, were sensitive to AZT and/or lamivudine, or marginal decreased sensitivity to one of these two drugs, referred to EC$_{50}$s obtained with recombinant variants (Table 2). These isolates were obtained from HIV-1 infected individuals who were either anti-HIV therapy naive or treated with the RT inhibitors. The isolates 3887 carried 184V substitution mixed with wt 184M, and the isolate 4877 had 41L mutation in the RTs. As shown in the Table 3, the EC$_{50}$s obtained using these four isolates for both DXG and prodrug DAPD are comparable to those observed with the

TABLE 3

Susceptibility of HIV-1 isolates from patients treated with nucleoside analogs to DXG and DAPD

| Viral Isolate | Antiviral Therapy (week) | RT genotype | $EC_{50}$ ($\mu M$) in CBMCs of: | | | |
|---|---|---|---|---|---|---|
| | | | DXG | DAPD | lamivudine | AZT |
| 3887 | Lamivudine (24) | 184 M/N | 0.18 ± 0.007 | 0.19 ± 0.12 | 0.11 ± 0.1 | 0.0007 ± 0.0003 |
| 4246 | AZT (104) | wt[a] | 0.12 ± 0.06 | 0.41 ± 0.02 | 0.023 ± 0.02 | 0.023 ± 0.017 |
| 4526[c] | Naive | ND[b] | 0.055 ± 0.027 | 0.85 ± 0.071 | ND | 0.0043 ± 0.005 |
| 4877[d] | Naive | 41L | 0.045± | 0.26± | ND | 0.015± |
| 3350 | Lamivudine (12) | 184V | 0.65 ± 0.33 | 3.3 ± 1.2 | >100 | 0.014 ± 0.01 |
| 4205 | Lamivudine (52) | 184V | 1.1 ± 1.19 | 4.1 ± 0.35 | >100 | 0.022 ± 0.014 |
| 4242 | AZT | 41L/70R/215Y | 0.21 ± 0.007 | 0.88 ± 0.3 | 0.009 | 0.15 ± 0.035 |
| 4833[c] | Saquinavir (48) | ND | 0.17 ± 0.06 | 0.63 ± 0.38 | ND | 0.062 ± 0.016 |
| 4924[d] | AZT/nevirapine (26) | 41L/103N | 0.02± | 0.17± | ND | 0.001± |

[a]wt, wild-type.
[b]ND, not determined.
[c]Both RT and protease genotypes were not determined. $EC_{50}$s for saquinavir were 0.0063 ± 0.0039 $\mu M$ against isolate 4526 and 0.11 ± 0.028 $\mu M$ against isolate 4833.
[d]$EC_{50}$s for nevirapine were 0.065 ± 0.001 $\mu M$ against isolate 4877 and >10 $\mu M$ against isolate 4924.

However, the isolate 4242 which was obtained from patient treated with AZT and carried AZT-resistance mutations, i.e. 41L/70R/215Y in RT, had decreased sensitivity to AZT as expected, but remained sensitive to DXG, DAPD as well as lamivudine. Assay used an NNRTI-resistant strain 4924 isolated from an individual received AZT and nevirapine combination therapy, which carried 41L/103N mutations in the RT and had >10 $\mu A$ $EC_{50}$ for nevirapine, was sensitive to the dioxolane nucleoside analogues (Table 3). In addition, the dioxolane compounds was also observed to be completely sensitive to the protease inhibitor-resistance isolate 4833 which was obtained from an individual received 48-week saquinavir therapy and had about 20-fold decreased sensitivity to this protease inhibitor compared to the baseline isolate 4526 (Table 3).

EXAMPLE 4

Combination Effects of DXG with Approved Anti-HIV-1 Agents

DXG, the active form of its prodrugs, was assessed through combinations with the approved anti-HIV-1 agents, i.e. NRTIs (AZT and lamivudine) and NNRTI (nevirapine) to inhibit HIV-1 replication in CBMCs against the laboratory strain HIV-1$_{IIIB}$. The combination indexes (Cis) of DXG combined with approved anti-HIV-1 agents are summarized in Table 4. The CIs were calculated at several effective concentration levels, i.e. $EC_{50}$, $EC_{75}$, $EC_{30}$ and $EC_{95}$, in different molar ratios of the combined drugs. The most of the CIs were between 0.4–0.8 in the case of DXG combined with either lamivudine or nevirapine, which suggest that DXG had moderate synergism with these two anti-HIV-1 agents. However, this compounds had greater synergism with thymidine analogue AZT with CIs between 0.3–0.8 at $EC_{50}$, and less than 0.3 at higher EC levels which indicates a strong synergism.

TABLE 4

Combination effect of DXG with approved anti-retroviral agents

| Drug Combination | Molar ratio | CI at Inhibition level in CBMCs | | | |
|---|---|---|---|---|---|
| | | $EC_{50}$ | $EC_{75}$ | $EC_{90}$ | $EC_{95}$ |
| DXG/AZT | 10:1 | 0.61 | 0.27 | 0.12 | 0.07 |
| | 20:1 | 0.57 | 0.29 | 0.15 | 0.10 |
| | 40:1 | 0.67 | 0.30 | 0.14 | 0.08 |
| | 80:1 | 0.78 | 0.37 | 0.18 | 0.11 |
| DXG/lamivudine | 1:1.6 | 0.79 | 0.59 | 0.47 | 0.41 |
| | 1.25:1 | 0.82 | 0.58 | 0.46 | 0.40 |
| | 2.5:1 | 0.74 | 0.52 | 0.42 | 0.38 |
| | 5:1 | 0.65 | 0.69 | 0.87 | 1.08 |
| DXG/nevirapine | 1.25:1 | 0.88 | 0.65 | 0.52 | 0.46 |
| | 2.5:1 | 0.90 | 0.64 | 0.52 | 0.46 |
| | 5:1 | 0.87 | 0.54 | 0.38 | 0.32 |
| | 10:1 | 0.95 | 0.57 | 0.38 | 0.31 |

EXAMPLE 5

Cellular Toxicity

DXG and DAPD along with lamivudine and AZT were tested for their effect on cell proliferation using both [$^3$H]-thymidine uptake and cell proliferation (WST-1) assays. Human PBMC and a number of established solid nd leukemic cancer cell lines (Molt-4, HT-1080, DU-145, HepG2) and one normal cell line (human skin fibroblasts, HSF) were used in the [$^3$H]-thymidine uptake study. The results from these studies showed that DXG and DAPD were non toxic to the cell proliferation up to a concentration of 500 $\mu M$ in the [$^3$H]-thymidine incorporation experiment (Table 5). In the same experiments, $CC_{50}$s for AZT and ddC had less than 10 $\mu M$ in the cells tested. In addition, DXG did not have toxicity to human CBMCs and several cell lines, i.e. MT-2, H9, Jurkat and U937, up to 100 $\mu M$, the highest concentrations tested in the WST-1 cell viability assay compared to the 74 $\mu M$ and 29 $\mu M$ of $CC_{50}$ for both AZT and ddC, respectively. Thus, DXG and DAPD were less cytotoxic than AZT and ddC in these assay systems.

TABLE 5

Effect of nucleoside analogs on cell proliferation in [$^3$H]-thymidine uptake assay

| | | | $CC_{50}$ ($\mu$M) | | |
|---|---|---|---|---|---|
| Cell | DXG[a] | DAPD[a] | lamivudine | AZT | ddC |
| PBMC | >500 | >500 | ND[b] | ND | 32.5 |
| Molt-4 | >500 | >500 | ND | 3 | 2 |
| HT-1080 | >500 | >500 | >500 | 5 | 2 |
| HepG2 | >500 | >500 | 350 | 3 | 7 |
| DU145 | >500 | >500 | >500 | >10 | 5 |
| HSF | ≧500 | >500 (350) | 400 | >10 | ND |

[a]The highest concentrations of DXG and DAPD used in these studies were 500 $\mu$M.
[b]ND, not determined.

EXAMPLE 6

Inhibition of HIV-1 RT Polymerase Activity by DXG Triphosphate

The DXG-TP would most likely be the antiviral active form for the diaminopurine dioxolane DAPD in vivo. The inhibitory effect of DXG-TP on HIV-1 RT activity was assessed using various homopolymeric template/primers (T/P) and a heteropolymeric T/P, i.e. HIV-PBS/dPR. The results from these experiments demonstrated that the DXG-TP was a potent HIV-1 RT inhibitor with 0.012 $\mu$M $IC_{50}$, obtained using wt HIV-1 RT when complementary poly(rC). oligo(dG) T/P and dGTP substrate were used in the enzymatic reactions (Table 6). This value has approximately the same inhibitory efficiency as the parental dideoxyguanosine triphosphate (ddGTP). Similarly, DXG-TP and ddGTP were observed to have the same inhibition of RT when the poly(rC), oligo(dG) was replaced by heteropolymeric template/primer HIV-PBS/dPR (Table 6). In addition, the RT inhibition of DXG-TP was observed to be competition with natural substrate, i.e. the higher the concentration of dGTP, the lower the inhibitory effect of DXG-TP. However, as expected DXG-TP did not show any inhibition of HIV-1 RT activity up to 10 $\mu$M when the non-complementary T/P poly(rA). oligo(dT) was used along with dTTP as the substrate. (Table 6).

TABLE 6

Inhibition of HIV-1 reverse transcriptase by DXG-TP and other dideoxynucleotide triphosphates

| | | $IC_{50}$ ($\mu$M) | | |
|---|---|---|---|---|
| Template/primer | Substrate | DXG-TP | ddGTP | ddTTP |
| poly(rC).oligo(dG)$_{12-15}$ | dGTP | 0.012 ± 0.002 | 0.011 ± 0.0007 | ND[a] |
| poly(rA).oligo(dT)$_{12-18}$ | dTTP | >10[b] | ND | 0.024 ± 0.003 |
| HIV-PBS/dPR | dNTPs[c] | 0.062 ± 0.007 | 0.074 ± 0.008 | ND |

[a]ND, not determined.
[b]The highest concentration or inhibitor used in the inhibition study was 10 $\mu$M.
[c]Each of the dATP, dCTP, dGTP and dTTP was 5 $\mu$M.

The chain elongation/termination assay provides a method to directly visualize the products of incorporation of dideoxynucleotide monophosphates into nascent DNA by monitoring the reaction products using polyacrylamide gel electrophoresis. The experiment was performed using wt HIV-1 RT, and HIV-PBS heteropolymeric template, and [$^{32}$p]ATP labeled dPR primer in the presence of various concentrations of RT inhibitor. The concentrations of the inhibitors used were 0, 0.7, 2.2, 6.6, 20, and 60 $\mu$M for DXG-TP, ddGTP and AZT-TP; 0, 1, 3, 10, 33, and 100 $\mu$M for 3TC-TP; 0, 0.005, 0.02, 0.08, 0.32 and 1.5 $\mu$M for NNRTI nevirapine. FIG. 2 shows results of a chain elongation/termination assay in which DXG-TP employed as HIV-1 RT inhibitor compared with other NRTI triphosphates, i.e. ddGTP, AZT-TP and lamivudine-TP, and a NNRTI nevirapine. The bands at the top of the gel were full-length DNA products of the RT reaction. In the lanes which reactions were absence of RT inhibitors, the remaining bands which were shorter than the full-length products are pausing products due to the fact that HIV-1 RT is a processive enzyme. The extra bands (indicated by arrows as examples) which are merely observed in the lanes in the presence of dideoxynucleotide triphosphate inhibitors are chain termination products. DXG-TP together with other nucleotides tested, i.e. ddGTP, AZT-TP and lamivudine-TP, caused increasing chain termination but decreasing full-length products with raising inhibitor concentration. As comparison, NNRTI nevirapine was also used in the assay. In this case, nevirapine also showed the decrease of the full-length DNA products, but there were no extra chain termination bands generated, as expected. These results reflect the different mechanisms of inhibition of the RT between NRTIs and NNRTIs.

Furthermore, the pattern of chain-termination bands generated by incorporation of DXG-MP into elongating DNA strands were exactly the same as pattern of its parental dideoxyguanidine (ddGMP) but different from thymidine and cytidine analogues, i.e. AZT-MP and lamivudine-MP incorporation (see FIG. 2). Generally, the inhibitory effect of DXG-TP on RT activity in this cell-free assay, determined by the intensity of the chain-termination and full-length bands generated , was the same as ddGTP and AZT-TP at the same concentrations, but higher than lamivudine-TP.

We claim:

1. A method of treating a patient infected with an HIV virus resistant to zidovudine, lamivudine and/or nevirapine, comprising administering to said patient an effective amount of (−)-β-D-2,6-diaminopurine and/or (−)-β-D-1,3-dioxolane and/or (−)-β-D-1,3-dioxolane guanine.

2. A method according to claim 1, wherein said patient is infected with an HIV virus resistant to zidovudine.

3. A method according to claim 1, wherein said patient is infected with an HIV virus resistant to lamivudine.

4. A method according to claim 1, wherein said patient is infected with an HIV virus resistant to nevirapine.

5. A method according to claim 1, wherein zidovudine, lamivudine and/or nevirapine is administered simultaneously with (−)-β-D-2,6-diaminopurine-1,3-dioxolane and/or (−)-β-D-1,3-dioxolane guanine.

6. A method according to claim 2, wherein zidovudine is administered simultaneously with (−)-β-D-2,6-diaminopurine-1,3-dioxolane and/or (−)-β-D-1,3-dioxolane guanine.

7. A method according to claim 3, wherein lamivudine is administered simultaneously with (−)-β-D-2,6-diaminopurine-1,3-dioxolane and/or (−)-β-D-1,3-dioxolane guanine.

8. A method according to claim 4, wherein nevirapine is administered simultaneously with (−)-β-D-2,6-diaminopurine-1,3-dioxolane and/or (−)-β-D-1,3-dioxolane guanine.

9. A method according to claim 6, wherein (−)-β-D-2,6-diaminopurine-1,3-dioxolane or (−)-β-D-1,3-dioxolane guanine and zidovudine are administered in a molar ratio of 10:1 to 80:1.

10. A method according to claim 7, wherein (−)-β-D-2,6-diaminopurine-1,3-dioxolane or (−)-β-D-1,3-dioxolane guanine and lamivudine in a molar ratio of 1:1.6 to 5:1.

11. A method according to claim 8, wherein (−)-β-D-2,6-diaminopurine-1,3-dioxolane or (−)-β-D-1,3-dioxolane guanine and nevirapine in a molar ratio of 1.25:1 to 10:1.

12. A method according to claim 1, wherein zidovudine, lamivudine and/or nevirapine is administered sequentially with (−)-β-D-2,6-diaminopurine-1,3-dioxolane and/or (−)-β-D-1,3-dioxolane guanine.

13. A method according to claim 2, wherein zidovudine is administered sequentially with (−)-β-D-2,6-diaminopurine-1,3-dioxolane and/or (−)-β-D-1,3-dioxolane guanine.

14. A method according to claim 3, wherein lamivudine is administered sequentially with (−)-β-D-2,6-diaminopurine-1,3-dioxolane and/or (−)-β-D-1,3-dioxolane guanine.

15. A method according to claim 4, wherein nevirapine is administered sequentially with (−)-β-D-2,6-diaminopurine-1,3-dioxolane and/or (−)-β-D-1,3-dioxolane guanine.

16. A method according to claim 13, wherein (−)-β-D-2,6-diaminopurine-1,3-dioxolane or (−)-β-D-1,3-dioxolane guanine and zidovudine are administered in a molar ratio of 10:1 to 80:1.

17. A method according to claim 14, wherein (−)-β-D-2,6-diaminopurine-1,3-dioxolane or (−)-β-D-1,3-dioxolane guanine and lamivudine in a molar ratio of 1:1.6 to 5:1.

18. A method according to claim 15, wherein (−)-β-D-2,6-diaminopurine-1,3-dioxolane or (−)-β-D-1,3-dioxolane guanine and nevirapine in a molar ratio of 1.25:1 to 10:1.

19. A pharmaceutical combination comprising (−)-β-D-2,6-diaminopurine-1,3-dioxolane or (−)-β-D-1,3-dioxolane guanine and zidovudine in a molar ratio of 10:1 to 80:1.

20. A pharmaceutical combination comprising (−)-β-D-2,6-diaminopurine1,3-dioxolane or (−)-β-D-1,3-dioxolane guanine and lamivudine in a molar ratio of 1:1.6 to 5:1.

21. A pharmaceutical combination comprising (−)-β-D-2,6-diaminopurine-1,3-dioxolane or (−)-β-D-1,3-dioxolane guanine and nevirapine in a molar ratio of 1.25:1 to 10:1.

22. A method according to claim 1, wherein an effective amount of (−)-β-D-2,6-diaminopurine-1,3-dioxolane is administered to said patient.

23. A method according to claim 2, wherein an effective amount of (−)-β-D-2,6-diaminopurine-1,3-dioxolane is administered to said patient.

24. A method according to claim 3, wherein an effective amount of (−)-β-D-2,6-diaminopurine-1,3-dioxolane is administered to said patient.

25. A method according to claim 4, wherein an effective amount of (−)-β-D-2,6-diaminopurine-1,3-dioxolane is administered to said patient.

26. A method according to claim 5, wherein an effective amount of (−)-β-D-2,6-diaminopurine-1,3-dioxolane is administered to said patient.

27. A method according to claim 6, wherein an effective amount of (−)-β-D-2,6-diaminopurine-1,3-dioxolane is administered to said patient.

28. A method according to claim 7, wherein an effective amount of (−)-β-D-2,6-diaminopurine-1,3-dioxolane is administered to said patient.

29. A method according to claim 8, wherein an effective amount of (−)-β-D-2,6-diaminopurine-1,3-dioxolane is administered to said patient.

30. A method according to claim 12, wherein an effective amount of (−)-β-D-2,6-diaminopurine-1,3-dioxolane is administered to said patient.

31. A method according to claim 13, wherein an effective amount of (−)-β-D-2,6-diaminopurine-1,3-dioxolane is administered to said patient.

32. A method according to claim 14, wherein an effective amount of (−)-β-D-2,6-diaminopurine-1,3-dioxolane is administered to said patient.

33. A method according to claim 15, wherein an effective amount of (−)-β-D-2,6-diaminopurine-1,3-dioxolane is administered to said patient.

34. A method according to claim 1, wherein an effective amount of (−)-β-D-1,3-dioxolane guanine is administered to said patient.

35. A method according to claim 2, wherein an effective amount (−)-β-D-1,3-dioxolane guanine is administered to said patient.

36. A method according to claim 3, wherein an effective amount of (−)-β-D-1,3-dioxolane guanine is administered to said patient.

37. A method according to claim 4, wherein an effective amount of (−)-β-D-1,3-dioxolane guanine is administered to said patient.

38. A method according to claim 5, wherein an effective amount of (−)-β-D-1,3-dioxolane guanine is administered to said patient.

39. A method according to claim 6, wherein an effective amount of (−)-β-D-1,3-dioxolane guanine is administered to said patient.

40. A method according to claim 7, wherein an effective amount of (−)-β-D-1,3-dioxolane guanine is administered to said patient.

41. A method according to claim 8, wherein an effective amount of (−)-β-D-1,3-dioxolane guanine is administered to said patient.

42. A method according to claim 12, wherein an effective amount of (−)-β-D-1,3-dioxolane guanine is administered to said patient.

43. A method according to claim 13, wherein an effective amount of (−)-β-D-1,3-dioxolane guanine is administered to said patient.

44. A method according to claim 14, wherein an effective amount of (−)-β-D-1,3-dioxolane guanine is administered to said patient.

45. A method according to claim 15, wherein an effective amount of (−)-β-D-1,3-dioxolane guanine is administered to said patient.

46. A method according to claim 22, wherein (−)-β-D-2,6-diaminopurine-1,3-dioxolane is at least 97% free of the corresponding (+) enantiomer.

47. A method according to claim 34, wherein (−)-β-D-1,3-dioxolane guanine is at least 97% free of the corresponding (+) enantiomer.

48. A method according to claim 1, wherein (−)-β-D-2,6-diaminopurine-1,3-dioxolane or (−)-β-D-1,3-dioxolane guanine is administered in an amount of 1–30 mg/kg/day.

* * * * *